United States Patent [19]

Tillery, Jr.

[11] Patent Number: 5,083,560

[45] Date of Patent: Jan. 28, 1992

[54] RESPIRATION MONITOR

[76] Inventor: Joe B. Tillery, Jr., 4066 Northview Dr., Jackson, Miss. 39206

[21] Appl. No.: 535,607

[22] Filed: Jun. 11, 1990

[51] Int. Cl.$^5$ .............................................. A62B 9/00
[52] U.S. Cl. ............................ 128/205.23; 128/207.14; 128/912
[58] Field of Search ...................... 128/205.23, 207.14, 128/207.16, 200.24, 202.22, 201.19, 911, 912, 207.15

[56] References Cited

U.S. PATENT DOCUMENTS

| | | | |
|---|---|---|---|
| 2,638,096 | 5/1953 | Waldhaus | 128/207.14 |
| 4,275,907 | 6/1981 | Hunt | 285/323 |
| 4,593,689 | 6/1986 | White | 128/207.15 |
| 4,911,157 | 3/1990 | Miller | 128/203.25 |

Primary Examiner—Edgar S. Burr
Assistant Examiner—Stephen R. Funk

[57] ABSTRACT

A respiration monitor adapted to be attached to an endotracheal tube whereby said monitor senses an animal breathing and emits an audible response directly corresponding to the depth, rate, force or absence of an animal's respiration.

3 Claims, 4 Drawing Sheets

RESPIRATION MONITOR

BACKGROUND OF THE INVENTION

The present invention relates to a respiration sensor or monitor, useful to veterinarians, for sensing or monitoring the breathing of animals following removal from a gas anesthetic machine.

A gas anesthetic machine is often used by small animal veterinarians while performing surgery on an animal. Typically, the gas anesthetic machine is attached to an endotracheal tube so that the animal receives sufficient anesthesia. Following surgery, the animal is detached from the anesthetic machine, thus allowing the animal to be moved to a recovery area. However, the endotracheal tube remains in the animal to prevent accidental aspiration and to maintain a clear, open and dry air passageway during recovery. Recovery may vary from several minutes to several hours.

While in recovery, the animal must be monitored so that the endotracheal tube can be removed when the cough reflex returns in order to prevent the animal from choking. Thus, either the veterinarian or a trained staff member must remain with the animal for the indefinite recovery period. It is, therefore, desirable for a means of monitoring or sensing the animal's breathing, or return of the cough reflex, so that the endotracheal tube can be removed to prevent the animal from choking.

Although the prior art includes numerous types of breathing sensors, these devices are often sophisticated or rely on electrical circuitry. The present invention contemplates a simple, inexpensive, lightweight monitor that plugs into the open end of an endotracheal tube and emits an audible response directly corresponding to the depth, rate and force, or absence of respiration. Such a device should also be capable of signaling the return of the cough reflex. A relief valve is also available so that the monitor can be tuned to obtain a maximum audible response depending on the size of the animal.

It is an object of the present invention to sense or monitor the breathing of an animal.

Another object of the present invention is to provide a device which is simple, inexpensive and lightweight and which is releasably attachable to an endotracheal tube.

An object of the present invention is to also emit an audible response corresponding to the depth, rate and force, or absence, of respiration.

It is also an object of the invention to be adjustable in order to tune the monitor to the breathing capacity of different size animals in order to obtain maximum response.

These and other objects of the present invention will become apparent upon review of the drawings and detailed description of the preferred embodiment.

DETAILED DESCRIPTION OF THE PREFERRED EMBODIMENT

Figure 1:
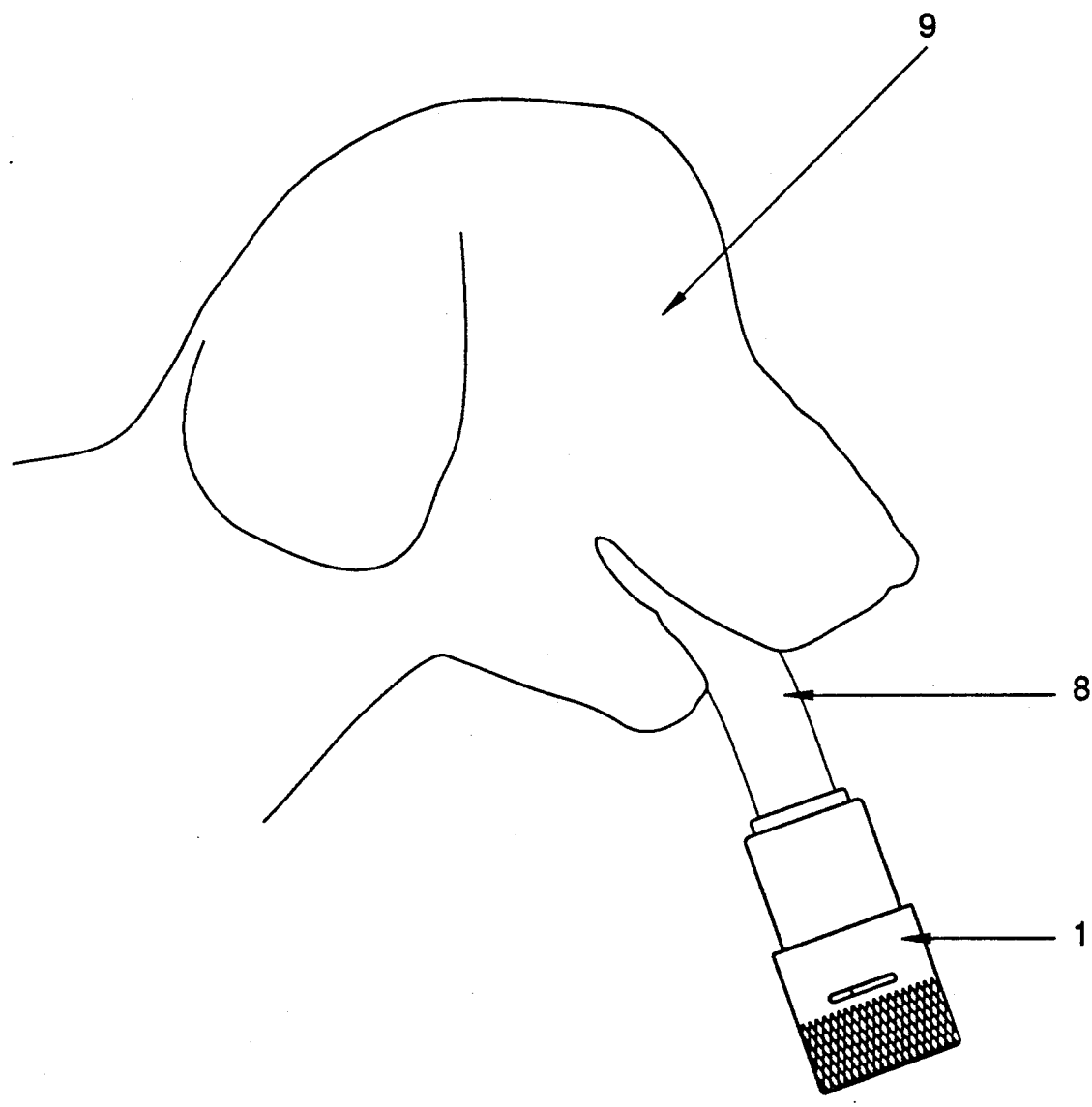
FIG. 1 is a view of the invention in relationship to an animal.

Referring to FIG. 1, the relationship of the invention to the animal can be seen. The invention 1 is releasably attached to the endotracheal tube 8 while the animal 9 is in recovery.

Figure 2:
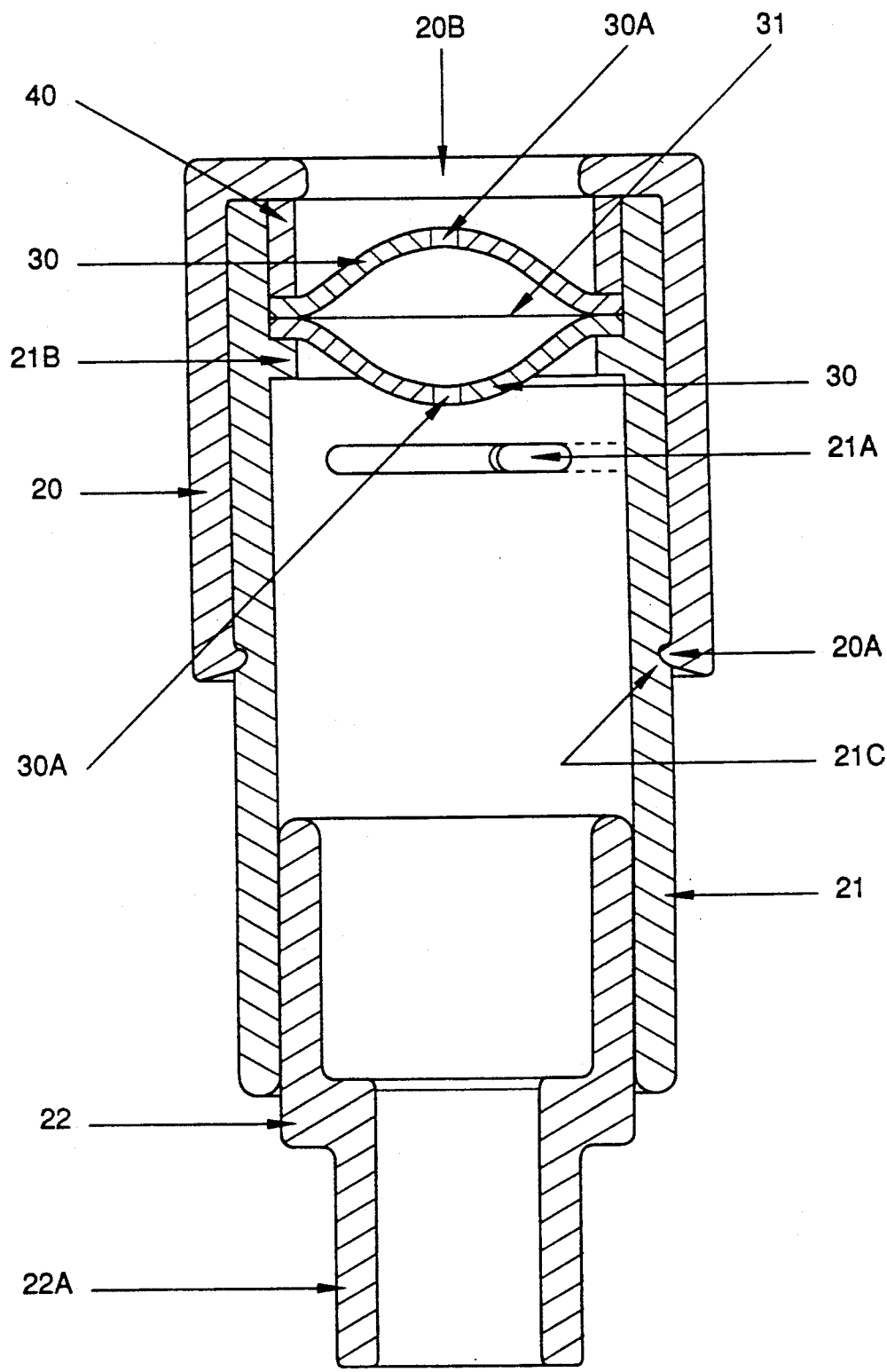
FIG. 2 is a longitudinal sectional view of the invention.
Figure 3:
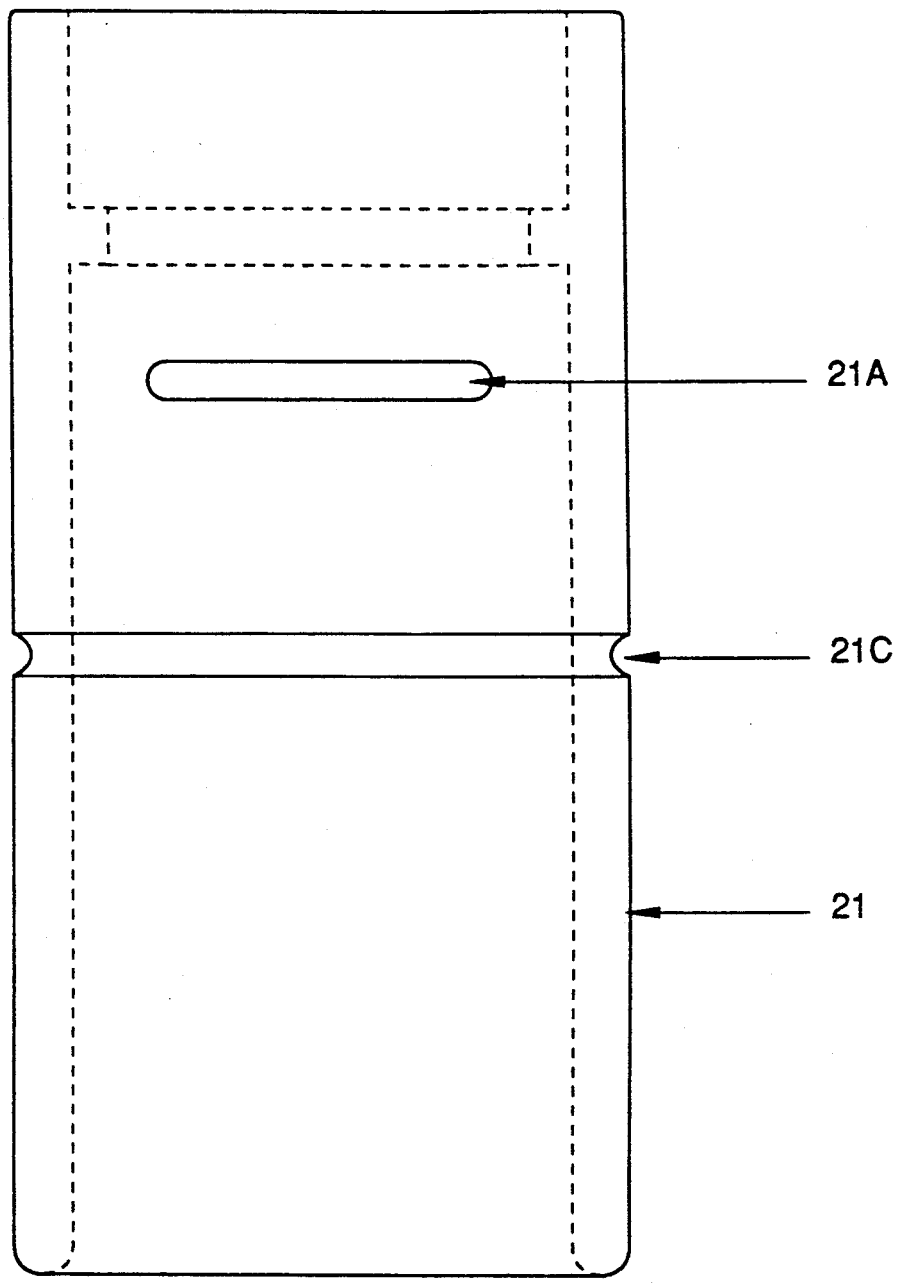
FIG. 3 is a side view of the cylindrical body portion of the invention.
Figure 4:
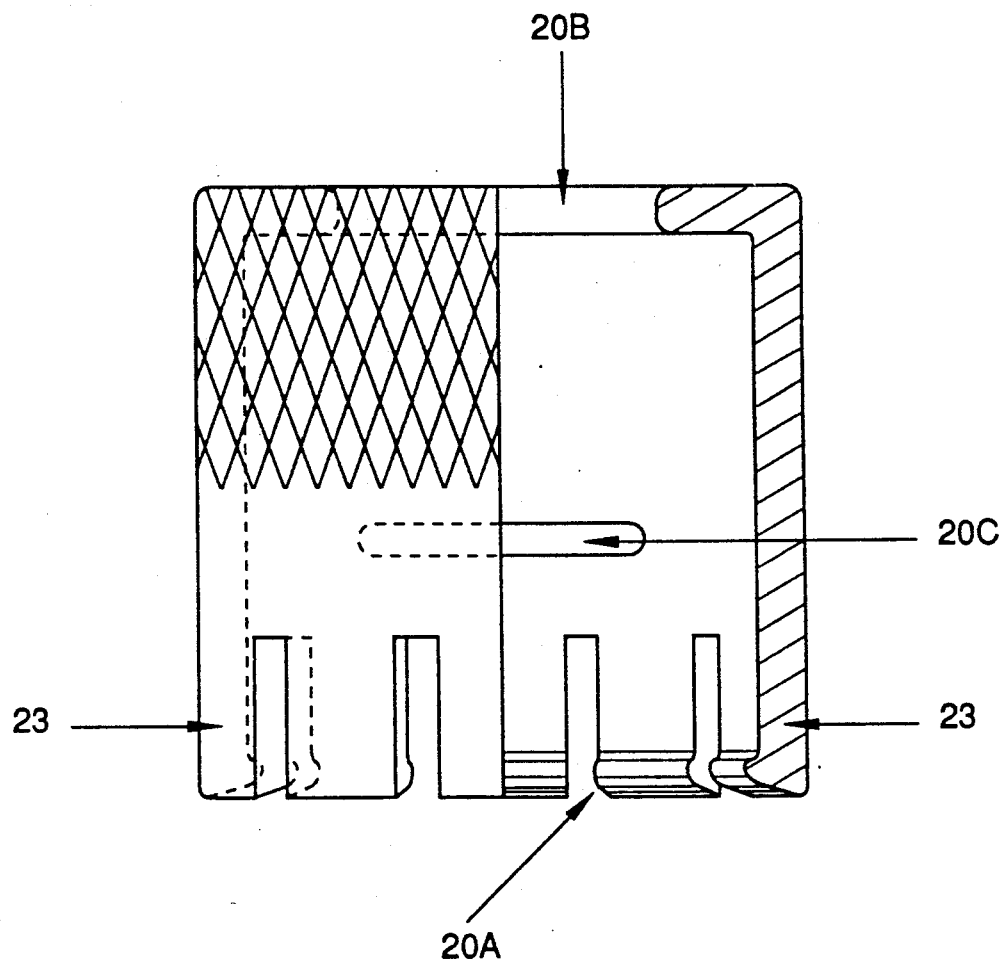
FIG. 4 is a side view of the outer housing portion of the invention.

Referring to FIGS. 2, 3 and 4, the invention 1 has a cylindrical body 21, a cylindrical outer housing 20, and an adapter member 22. Said adapter 22 is slidably insertable into the inner diameter of the main body 21. The end 22a of the adapter 22 is slidably insertable into the inner diameter of the endotracheal tube 8. Thus, the invention is readily attachable to the animal while in recovery.

The body 21 forms a recess 21c around its outer diameter for accepting a multiplicity of projection members 20a located at the end of each finger 23 of said housing 20. This arrangement allows the housing 20 to be slid over the body 21 until the projection members 20a engage the recess 21c in order to releasably secure the housing 20 to the body 21.

In addition to the outer elements of the invention, there are certain inner elements which make the invention operable. These inner elements consist of a plurality of sound discs 30 and a retainer 40. It should be noted that each sound disc 30 forms a hole 30a on its outermost side. When assembled as shown in FIG. 2, the discs 30 are adjacent to each other as indicated by number 31. The sound discs 30 are then held in place by the retainer 40, the ledge 21b of the body 21, and the housing 20.

Once the invention is assembled, it should be noted that the slot 21a in the body 21 can be aligned with the slot 20c located in the housing 20. This alignment is best shown in FIG. 2.

Thus, by simply rotating the housing 20, the slots 20c and 21a may be aligned so as to increase or decrease the air supply within the passageway of said main body 21 and thereby tune the invention to the breathing capacity of different size animals in order to obtain the maximum audible response.

When it is desired to use the invention, the end 22a of the adapter member is slid into the endotracheal tube 8 leading from the animal 9. In this position, as the animal breathes, air flows through the passageway of the adapter 22, into the main body 21, where it passes through the hole 30a in the lower sound disc 30 and out of the hole 30a in the upper sound disc 30. The flow of air through the holes 30a therefore results in an audible noise being emitted out of the opening 20b of the housing 20. By operating in this manner, the loudness and length of the audible noise emitted by the sound discs 30 are proportional to the rhythm and length of breath of the animal.

Once the endotracheal tube is removed from the animal, the invention is then slidably released from the endotracheal tube. By removing the outer housing from the cylindrical body, the inner assembly pieces of the invention can be removed and each component sterilized and cleaned.

The present invention has been described in detail with particular reference to the preferred embodiments thereof, but it will be understood that variations and modifications can be effected within the spirit and scope of the invention as described and a defined in the appended claims.

What I claim is:

1. A breathing sensor comprising, a cylindrical body forming a first passageway for the flow of air;

a cylindrical outer housing forming a second passageway for the flow of air, said housing being releasably attached to the cylindrical body;

a plurality of sound discs releasably secured to the inner diameter of said cylindrical body; and a means for releasably connecting said cylindrical body to an endotracheal tube;

and a means to adjust the flow of air through the passageways, said means including a longitudinal slot in each of said cylindrical outer housing and said cylindrical body, said cylindrical outer housing and said cylindrical body being rotatable relative to each other so as to adjust the extent to which said slots overlap and thereby the flow of air through the passageways.

2. The apparatus of claim 1 wherein said housing includes a multiplicity of finger members having a ridge on their innermost diameter and said cylindrical body includes a recess around its outermost diameter for accepting said ridges so that said ridges will releasably engage said recess to secure said housing to said body.

3. A breathing sensor comprising, a cylindrical body forming a first passageway for the flow of air, said body forming a longitudinal slot therein, and said body having a recess around its outermost diameter;

a cylindrical outer housing forming a second passageway for the flow of air, said housing being releasably attachable to the outer portion of said cylindrical body, said body forming a longitudinal slot therein so that when said housing is releasably secured to said body, said slots may be aligned so as to vary the air flow through the passageways formed by said cylindrical body, said housing having a multiplicity of finger members each having a ridge on its innermost diameter for engaging the recess around the outermost diameter of said body;

a plurality of sound discs releasably secured to the inner diameter of said cylindrical body; and a means for releasably connecting said cylindrical body to an endotracheal tube.

* * * * *